(12) United States Patent
Matsuda

(10) Patent No.: US 11,576,804 B2
(45) Date of Patent: Feb. 14, 2023

(54) ORTHOTIC APPLIANCE

(71) Applicant: NAKAME, INC., Tokyo (JP)

(72) Inventor: Hiroshi Matsuda, Tokyo (JP)

(73) Assignee: NAKAME, INC., Tokyo (JP)

( * ) Notice: Subject to any disclaimer, the term of this patent is extended or adjusted under 35 U.S.C. 154(b) by 151 days.

(21) Appl. No.: 16/337,497

(22) PCT Filed: Oct. 2, 2017

(86) PCT No.: PCT/JP2017/035887
§ 371 (c)(1),
(2) Date: Jun. 3, 2019

(87) PCT Pub. No.: WO2018/062569
PCT Pub. Date: Apr. 5, 2018

(65) Prior Publication Data
US 2019/0282388 A1  Sep. 19, 2019

(30) Foreign Application Priority Data

Sep. 30, 2016 (JP) .............................. JP2016-193239

(51) Int. Cl.
*A61F 5/01* (2006.01)
*A61F 13/06* (2006.01)
(Continued)

(52) U.S. Cl.
CPC ................ *A61F 5/019* (2013.01); *A61F 5/01* (2013.01); *A61F 5/37* (2013.01); *A61F 13/06* (2013.01); *A63B 71/08* (2013.01)

(58) Field of Classification Search
CPC .... A61F 5/01; A61F 5/019; A61F 5/02; A61F 5/10; A61F 13/06; A61F 13/063;
(Continued)

(56) References Cited

U.S. PATENT DOCUMENTS 9,066,790 B1 * 6/2015 Fisher .................... A61F 5/019
2001/0047146 A1  11/2001 Toda
(Continued)

FOREIGN PATENT DOCUMENTS

CN          1520796 A      8/2004
CN        204838307 U     12/2015
(Continued)

OTHER PUBLICATIONS

Machine Translation of Publication No. KR200393008Y1 created Mar. 23, 2021 from Espace.net (Year: 2005).*
(Continued)

*Primary Examiner* — Ophelia A Hawthorne
*Assistant Examiner* — Gina McCarthy
(74) *Attorney, Agent, or Firm* — Renner, Otto, Boisselle & Sklar, LLP

(57) ABSTRACT

Provided is an device for stabilizing the center of gravity and/or correcting distortion of the body simply through wearing of the appliance on a toe and conducting normal activities. The following invention is provided by the present invention. A cylindrical correction device that corrects distortion of the body, wherein: the correction device has inward-facing triangular-prism-shaped protrusions on the inner circumference; the triangles are inclined in one direction with respect to the circumference; and the correction device comprises a cylindrical elastic material having a diameter of 7-20 mm, a width of 5-10 mm, a thickness of 1-3 mm, and a hardness of 4-6.

2 Claims, 10 Drawing Sheets

A

B

(51) Int. Cl.
*A63B 71/08* (2006.01)
*A61F 5/37* (2006.01)

(58) Field of Classification Search
CPC ...... A61F 13/064; A61F 13/068; A61F 13/10; A61F 2013/0048; A61H 39/04; A61H 7/00; A61H 7/001; A61H 7/002; A61H 2205/125; A61H 11/00; A63B 71/08; A44C 9/00; A44C 15/0085; A44C 15/009; A61B 17/132; A61B 17/12
See application file for complete search history.

(56) References Cited

U.S. PATENT DOCUMENTS

| | | | |
|---|---|---|---|
| 2010/0222728 A1* | 9/2010 | Brooks | A61F 13/068 602/30 |
| 2017/0231806 A1 | 8/2017 | Matsuda | |

FOREIGN PATENT DOCUMENTS

| | | |
|---|---|---|
| CN | 205598061 U | 9/2016 |
| JP | 8-182716 A | 7/1996 |
| JP | 10-234757 A | 9/1998 |
| JP | 3132615 U | 5/2007 |
| JP | 3132615 U * | 6/2007 ............... A61F 5/10 |
| JP | 2007-167122 | 7/2007 |
| JP | 2010115464 | 5/2010 |
| JP | 2015177962 | 10/2015 |
| KR | 200393008 Y1 * | 8/2005 |
| KR | 100679104 B1 | 2/2007 |
| KR | 20110030137 A | 3/2011 |
| WO | WO 1998/057602 A1 | 12/1998 |
| WO | 2016024420 A1 | 2/2016 |
| WO | WO 2016/024420 A1 | 2/2016 |
| WO | WO 2016/024638 A1 | 2/2016 |

OTHER PUBLICATIONS

Machine Translation of Publication No. JP3132615U created Apr. 21, 2022 from Google Patents [retrieved from ttps://patents.google.com/patent/JP3132615U/en?oq=JP3132615U] (Year: 2007).*

Machine Translation of Publication No. KR200393008Y1 created Dec. 10, 2022 from Espace.net (Year: 2005) (Year: 2005).*

Machine Translation of Publication No. JP3132615U created Apr. 21, 2022 from Google Patents [retrieved from ttps://patents.google.com/patent/JP3132615U/en?oq=JP3132615U] (Year: 2007) (Year: 2007).*

International Search Report for related International Application No. PCT/JP2017/035887 dated Dec. 20, 2017.

* cited by examiner

[Fig.1]
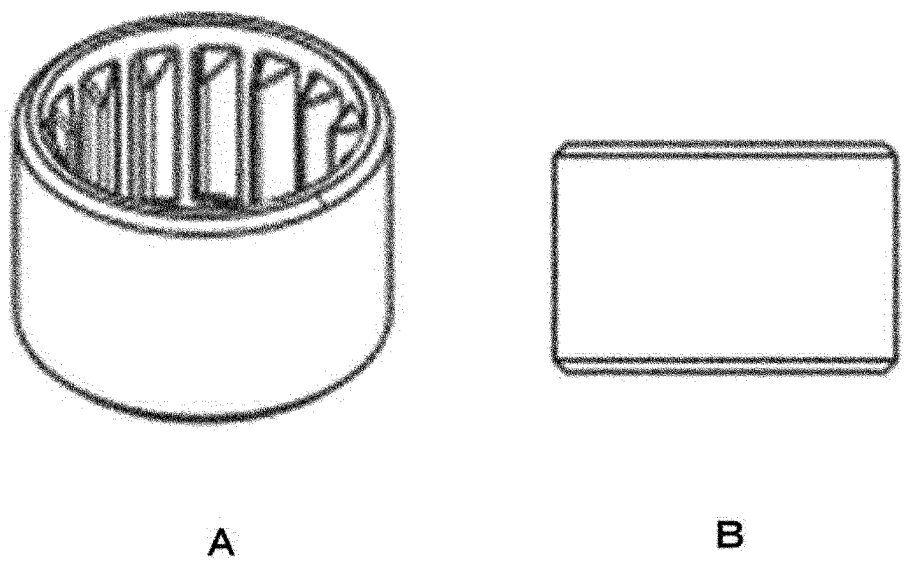
A　　　　　　　　　　B

[Fig.2]
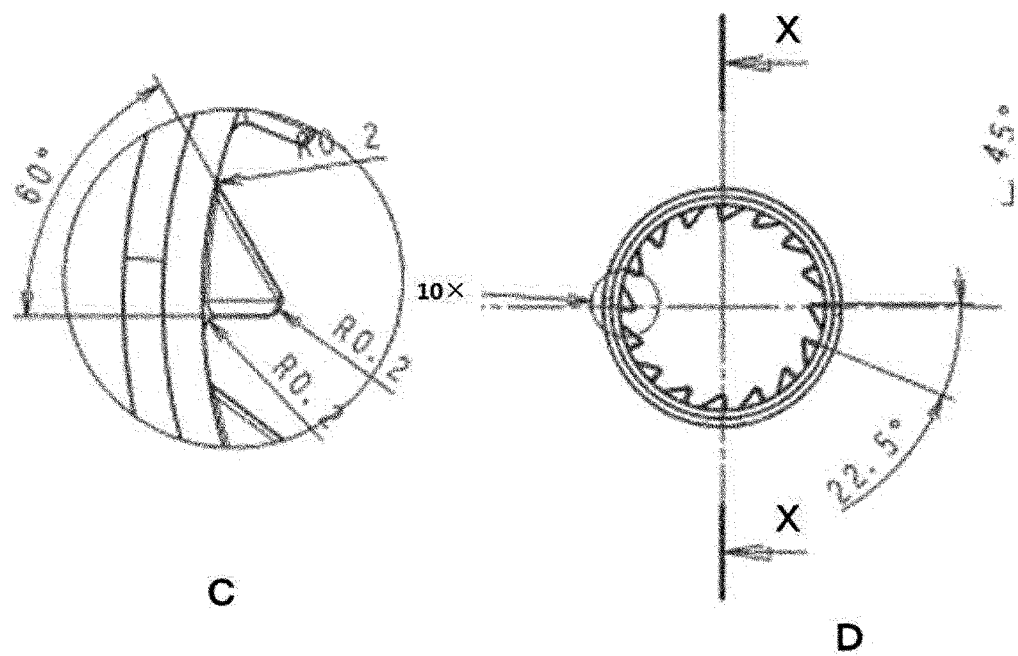

[Fig.3]
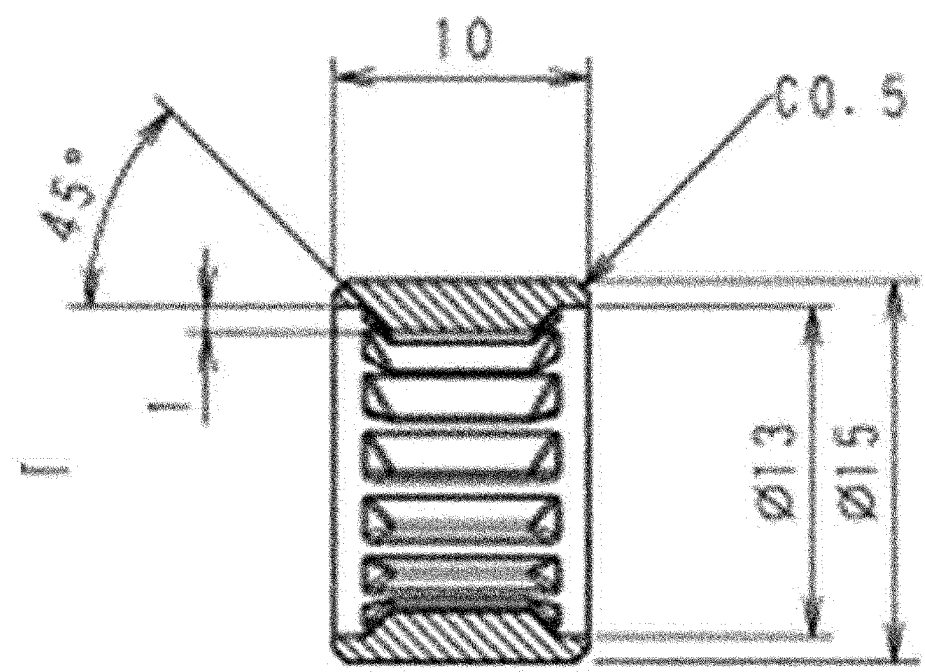

[Fig.4]
| before wearing | after wearing |
|---|---|
|  |  |
|  |  |

[Fig.5]
| before wearing | after wearing |
|---|---|
|  |  |
| 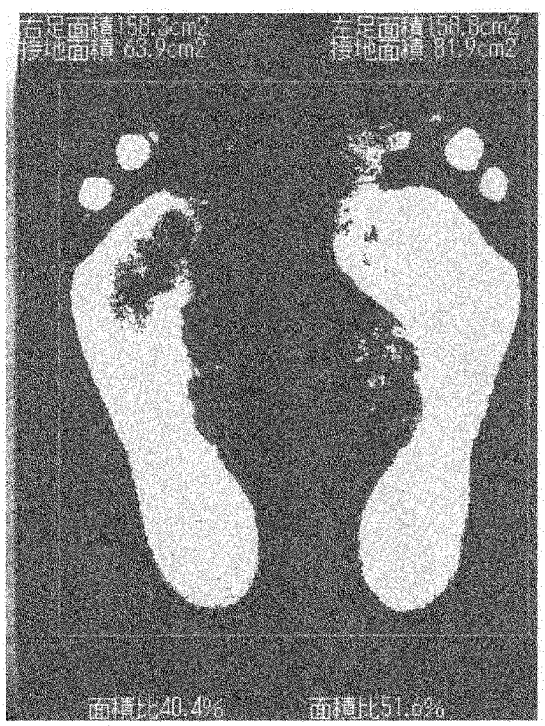 |  |

[Fig.6]
| before wearing | after wearing |
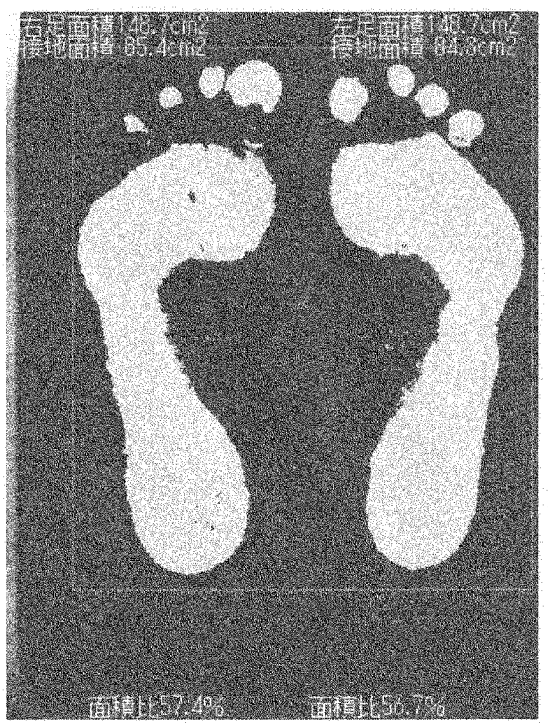
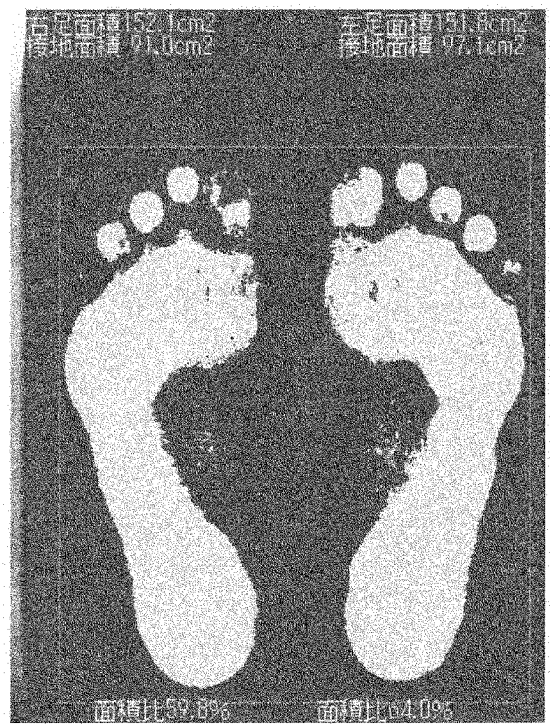

[Fig.7]
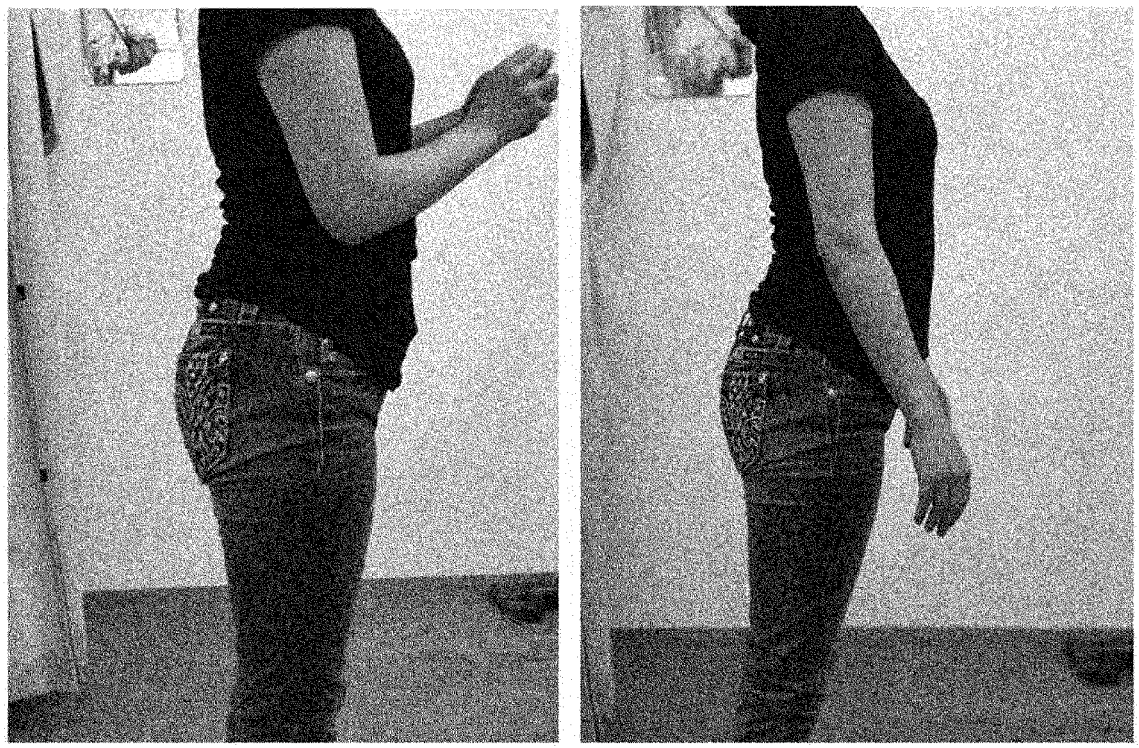

[Fig.8]

[Fig.9]
 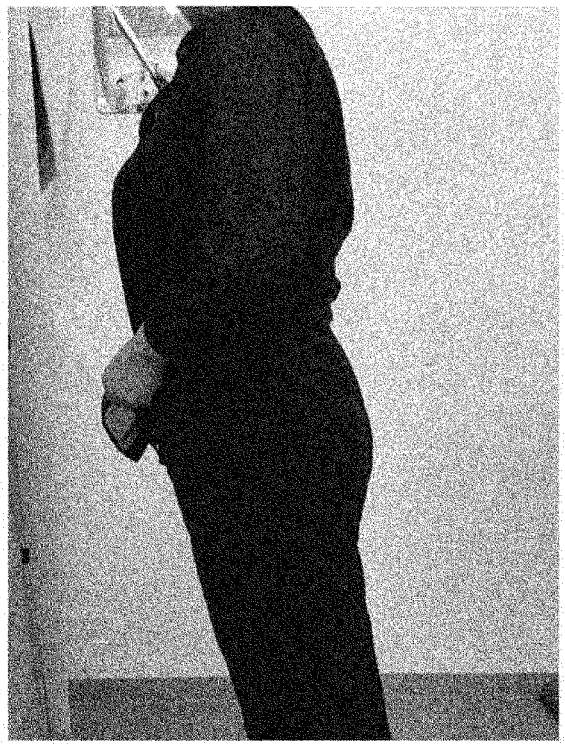
subject A before wearing   subject A after wearing

[Fig.10]
before wearing	after wearing

ORTHOTIC APPLIANCE

TECHNICAL FIELD

The present invention relates to a correction device for improving body distortion.

BACKGROUND ART

In recent years, with the westernization of lifestyles, there are less opportunities to sit straight in daily life, but there still remain to some extent. In addition, with the development of transportation in recent years, the number of people with a lack of exercise has increased, and there is an increasing opportunity for body distortion due to office work with an unnatural posture. These body distortions may cause unnatural landing on the foot, dislocate the center of gravity, and may further deteriorate body distortion.

As a device for removing such distortion of the body, the support ring for toes of Patent Document 1 is known. But it is a complicated shape, and it is attached only to the thumb of the foot, and always keeps the posture by making the toes conscious. However, there is a problem that it is difficult to keep it on for a long time with paying attention to the toes all the time.

In addition, a toe band which has no sense of wearing even when attached on a daily basis has also been developed (Patent Document 2). However, in this case, it was necessary to attach a band to a plurality of toes.

Therefore, there has been a demand for an invention which can be kept attached and in which the number of toes attached can be reduced.

RELATED ART DOCUMENTS

Patent Documents

Patent literature 1: Japanese Unexamined Patent Application Publication No. 2007-167122
Patent literature 2: WO2016/024420

SUMMARY OF THE INVENTION

Problem to be Solved by the Invention

The present invention provides a device that can be worn and have a normal life to stabilize the center of gravity, to improve flexibility, and/or to correct body distortion.

Means for Solving the Problem

According to the present invention, the following inventions are provided.

(1) A cylindrical correction device, which has a triangular prism-like protrusion into an inner direction on the inner peripheral portion, and triangles are inclined in one direction with respect to a circumference. Here, the triangular prism-like means that the side in contact with the inner circumference is in an arc shape in accordance with the inner circumference of the cylinder. Also, the bottom surface of the triangular prism-like protrusion may be parallel to the vertical cutting surface of the cylinder, or may be inclined from the vertical cutting surface of the cylinder to the inside (lower side at upper base, upper side at bottom base) of the cylinder.

(2) The correction device according to (1), wherein the triangular prism is parallel to the axial direction of the cylinder. Here, the axial direction means parallel to the axis passing through the center of the cylinder (cylinder). In this case, it is most preferable that they are completely parallel, but they may have an angle ±10% or less, more preferably ±5% or less, more preferably ±3% or less, still more preferably ±1% or less with respect to the axis.

(3) The correction device according to (1) or (2), wherein the cylindrical shape is made of a cylindrical elastic material having a diameter of 7 to 20 mm, a width of 5 to 10 mm, a thickness of 1 to 3 mm and a hardness of 4 to 6. Here, the hardness refers to the hardness measured by a hardness tester called Type A durometer based on the standard of JIS K6253. Moreover, as a elastic material, it is listed, but not limited to, rubber gum, and a silicone rubber, etc. Preferably it is silicone rubber.

(4) The correction device according to any one of (1) to (3), wherein the flexibility of the body is improved by wearing it. Here, the term "flexibility" refers to asymmetric flexibility such as being hard to bend in one direction. For example, it refers to the difference in flexibility depending on the direction, such as bending in front considerably, but bending in back does not bend at all. This is considered to be due to the distortion of the body.

(5) The correction device according to any one of (1) to (3), characterized in that bow legs and spine distortion, pelvis distortion and center of gravity shift are corrected by wearing it.

(6) A method for reducing or treating one or more symptoms selected from the group consisting of bow legs, spine strain, pelvic strain, and center of gravity shift using the correction device of any of (1) to (4). In addition, although this method is effective also to humans, it is also applicable to symptom reduction and treatment of animals other than humans (for example, pets such as dogs).

(7) The correction device according to any one of (1) to (4), characterized by lifting buttocks by wearing it.

(8) A method of lifting buttocks using any one of the correction devices of (1) to (4).

Effects of the Invention

According to the present invention, wearing the device of the present invention has the effect of improving the flexibility.

BRIEF DESCRIPTION OF DRAWINGS

FIG. 1 is a perspective view (A) and a side view (B) of a correction device (a toe band) of the present invention.

FIG. 2 is a protrusion (C) and a top view (D) provided on the inner periphery of the toe band of the present invention.

FIG. 3 is a view showing a cross-sectional view in the case of being cut by X in FIG. 2D.

FIG. 4 shows a pressure distribution map of the soles before and after wearing the toe bands of the present invention.

FIG. 5 shows pressure distribution maps of the soles before and after wearing the toe bands of the present invention.

FIG. 6 shows pressure distribution maps of the soles before and after wearing the toe bands of the present invention.

FIG. 7 is a side view of a state of buttocks lift after wearing the toe band of the present invention.

FIG. 8 is a side view of a state of buttocks lift after wearing the toe band of the present invention.

FIG. 9 is a side view showing a state of buttocks lift after attaching the toe band of the present invention.

FIG. 10 is a photograph showing a state of buttocks lift after wearing the toe band of the present invention viewed from behind.

DESCRIPTION OF EMBODIMENTS

The toe band of the present invention has a function of correcting the deviation of the center of gravity of the body. As a result, body distortion is corrected and flexibility is increased.

In the toe band of the present invention, the outer surface (peripheral surface) of the cylinder is preferably free from attachments such as protrusions, and the outer periphery of a flat cylinder is preferable. With the flat outer peripheral surface, it is possible to live without being aware of wearing, without affecting other fingers by pressure or the like.

On the inner side (inner peripheral part) of the cylinder, protrusions having a shape close to a triangular prism are arranged at a uniform distance. This triangle is aligned so that it is easy to twist in one direction after mounting the correction device (FIG. 2D). That is, the shape of the bottom of the triangular prism is not an isosceles triangle, but the vertex is deviated either from the vertex of the isosceles triangle, and the direction of the deviation is single direction for all triangles. Such a triangle (the base of a triangular prism) may be, for example, but not limited to, a right triangle and a triangle having an inner vertex of about 60 degrees. Preferably, the triangular prism is disposed in the same direction as the direction of the opening of the toe band, that is, in the direction perpendicular to the circumference. However, the angle with respect to the circumference does not have to be strictly perpendicular, and may be within ±5 degrees, more preferably ±3 degrees, still more preferably ±2 degrees, and most preferably ±1 degree from the right angle.

The number of triangular prismatic protrusions per cylinder is preferably at least any of 3, 4, 5, 6, 7, 8, 9, 10, 11, 12, 13, 14, 15. The upper limit of the number of triangular prismatic protrusions is preferably any of, 30 or less, 29 or less, 28 or less, 27 or less, 26 or less, 25 or less, 24 or less, 23 or less, 22 or less, 21 or less, 20 or less, 19 or less, 18 or less, and 17 or less.

The size of the triangular protrusion is preferably 0.5 mm or more, 1.0 mm or more, 1.5 mm or more at a distance from the inner circumferential surface toward the center, and as an upper limit, 3 mm or less, 2.5 mm or less, and 2.0 mm or less are preferable.

The upper limit of the angle of the protrusion protruding into the inside of the triangle is preferably 80 degrees or less, 75 degrees or less, 70 degrees or less, 65 degrees or less, and most preferably 60 degrees. The lower limit of the angle of the projections is 30 degrees or more, 40 degrees or more, 45 degrees or more, 50 degrees or more, 55 degrees or more, and most preferably 60 degrees. The angle may be the same for all the protrusions, or may be different for each protrusion, but preferably substantially the same. Substantially identical means, for example, at 60 degrees, preferably within 60 degrees ±3 degrees, more preferably within ±2 degrees, further preferably within ±1 degree. The same is true for other angles.

The apex of the inward protrusion of the triangular prism may be acute or may be slightly rounded to avoid pain (see FIG. 2C).

When the toe band of the present invention was worn, the flexibility was observed to be improved. Moreover, compared to a simple toe band, the effect was recognized even if the number of fingers to be worn was small.

The correction device of the present invention is a cylindrical device made of an elastic material. Although the size is not particularly limited, one having a diameter of 7 to 20 mm, a width of 5 to 10 mm, a thickness of 1 to 3 mm and a hardness of 4 to 6 is preferably used. More preferably, it has a diameter of 8 to 16 mm, a width of 6 to 8 mm, a thickness of 2 mm, and a hardness of 5, but it may have a larger shape for large people or foreigners. In addition, in the case of playing a rough sport, a higher hardness may be used. The basic form is shown in FIGS. 1 and 2. It is also possible to perform anti-slip processing such as embossing on a portion (triangle) that touches the inside finger.

The material having elasticity is not particularly limited as long as it is a material that is flexible and deformable and stretchable, but, for example, various elastomer resins etc. such as urethane resin, butadiene rubber, styrene-butadiene rubber, styrene-acrylonitrile rubber, isoprene rubber, ethylene vinyl acetate polymeric rubber, chloroprene rubber, natural rubber, silicone gel, silicone rubber, acrylic rubber, and styrene rubber, and the like are preferably used. Among these, silicone rubber is particularly preferable in consideration of wearing feeling, color and the like. The point is that it should be a material that is appropriately compressed when put on the toes, and has elasticity that does not bother even if it is worn all day. Moreover, the material may consist of only one kind material or may comprise combination of plural kinds of materials.

The elastic material may include an antibacterial agent. As the antibacterial agent, an antibacterial agent well known to those skilled in the art can be used, and it is not particularly limited. For example, a silver based antibacterial agent (such as zeolite zirconium, apatite, or Titania carrying silver ions) can be used. The antimicrobial agent is preferably blended in an amount of 0.01 to 10% by weight based on the total rubber component, and more preferably 0.1 to 5% by weight.

Here, "made of a material having elasticity" means that the material having elasticity is included as a main component and does not mean it does not include the material without elasticity at all. Some non-elastic materials may be included.

The color is preferably transparent to translucent, and when colored, a color close to the skin color and inconspicuous is preferable but is not limited thereto. For example, colorful items or patterns may be added to use as a fashion.

In the correction device of the present invention, the whole cylinder surface of the cylindrical form may be continuous or may have a hole like a mesh. The point is that the shape of the cylinder is not particularly limited as long as the body distortion is corrected by wearing.

The correction device of the present invention is used by being worn to one or more of the toe, i.e., the toe, the forefinger, the middle finger, the ring finger, and the little finger. Under the present circumstances, it may be worn with left-right symmetry, but it may be worn asymmetrically according to a patient's case. Further, the number of devices to be worn may not be the same, and for example, there may be a case where the flexibility is improved even with only one right foot finger. In addition, when the right foot ring finger and the left foot little finger, the right foot ring finger and the right foot little finger, and the left foot ring finger and the left foot little finger were worn, improvement in flexibility was observed (Table 1).

It is preferable that the finger is worn to a toe which changes in body flexibility or the like when actually be worn. For example, it is preferable to wear it on the toe where the hand is difficult to touch the floor when bending forward. The point is, it may be worn on the toes where effects such as increased flexibility are felt when worn.

Usually, the toe bands are worn on the toes of both feet, and are worn on toes which are selected as particularly effective toes, not all toes. Due to the tendency of body distortion, it is also effective to receive expert advice that is known empirically as to which finger to wear.

The cases to which the correction device of the present invention is applied are not particularly limited, but it is suitably used for people with cases such that the center of gravity is shifted, that the body flexibility is low, knee joint pain, bow legs, X leg, spine distortion, cervical spine distortion, low back pain etc. The distortion of the body is easily found by the median line shift when observed at the body in an upright position. When the center of gravity is shifted, the center line of the body is shifted to the left or right from the midline. Also, whether the center of gravity is out of place can be determined by inserting a sheet of paper or the like on the sole of the foot to see if there is a gap. By observing these, it is possible to select an appropriate toe for wearing the correction device of the present invention.

According to the correction device of the present invention, since the degree of application of force to the toes can be adjusted, the weight is placed on the entire sole of the foot, the center of gravity is stabilized, and thus the distortion of the body is corrected. Therefore, flat feet, hallux valgus, etc. can also be corrected. People with hip pain who was hard to put feet on the floor became able to put weight on the entire sole of the foot by wearing the correction device of the present invention.

Although the mechanism by which the correction device of the present invention is effective has not been fully elucidated yet, it is conceivable that so-called meridians may be involved. The correction device (torsion band) of the present invention can not only stimulate but also suppress meridians by the direction of insertion. A flat band with a smooth surface (WO 2016/024420) could only stimulate the meridians to relax the muscles involved. The correction device of the present invention is characterized in that it can not only stimulate the meridians (relaxing the muscles) but also suppress the meridians and tension the muscles. Therapeutic effects can be exerted not only on chronic pain, but also on chronic diseases because stimulation and suppression become possible. Furthermore, the toe band of the present invention also has an effect that the effect is quicker than the so-called treatment method using a pressure point, in terms of exerting effects from the moment of putting it on.

About the direction of clockwise or counterclockwise, the wearing way for tension or relaxation is determined by the meridians of yang and yin. Because the center of gravity is shifted toward the tense side, if the tension and relaxation of related muscles can be manipulated, shift of the center of gravity balance can be manipulated with certainty.

The correction device of the present invention is also effective for correcting the center of gravity of not only humans but also non-human animals. For example, when the limping dog labrador was worn with the correction device of the present invention, it became easy to ascend and descend stairs. In this case, it is preferable for the owner to put on and take off the correction devices without leaving the device worn.

Wearing the correction device of the present invention (also referred to as a twisting band or toe band) enables buttocks lift. When nine female subjects were worn with the correction device of the present invention, all had subjective feeling of buttocks lift. It turned out that it was buttocks lift even others surrounding see it (refer Table 2 and FIGS. 7-10).

The present invention will be described below using examples, but the present invention is not limited by the following examples.

EXAMPLES

Example 1

The distance from the floor at forward bending was measured for 5 women and 3 men before and after wearing the toe band of the present invention. The toes involved in body flexion are the ring finger and the little finger. The wearing finger was determined according to the distortion of each person's body. The direction of twisting the toe band is the direction of the little finger toward the instep side of the foot. The results are shown in Table 1.

TABLE 1

| | | | | | forward bending result (cm) | | | |
| | | | | | before wearing | | after wearing | |
| subject | age | sex | wearing position | direction of twist | left | right | left | right |
|---|---|---|---|---|---|---|---|---|
| 1 | 41 | female | right foot ring finger | Instep side little finger direction | ±0 | ±0 | −7 | −7 |
| 2 | 41 | female | right foot ring finger left foot little finger | Instep side little finger direction | 12 | 11 | −11 | −11.5 |
| 3 | 46 | female | right foot ring finger right foot little finger | Instep side little finger direction | −5 | −5 | −10 | −10 |
| 4 | 47 | female | right foot ring finger | Instep side little finger direction | −7 | −7 | −11 | −13 |
| 5 | 57 | female | left foot ring finger left foot little finger | Instep side little finger direction | 6 | 5 | −6 | −6 |

TABLE 1-continued

| | | | | | forward bending result (cm) | | | |
|---|---|---|---|---|---|---|---|---|
| | | | wearing | direction of | before wearing | | after wearing | |
| subject | age | sex | position | twist | left | right | left | right |
| 6 | 38 | male | left foot ring finger left foot little finger | Instep side little finger direction | 13 | 12 | 7 | 6.5 |
| 7 | 40 | male | left foot ring finger left foot little finger | Instep side little finger direction | 18 | 17 | 13 | 12 |
| 8 | 44 | male | right foot ring finger right foot little finger | Instep side little finger direction | 10 | 11 | −4 | −5 |

As shown in Table 1, in women, the flexibility was improved at a minimum of 7 cm (subject 1) and at most 23 cm (subject 2). In the case of men, the flexibility was improved at least 5 cm (subject 6) and at most 16 cm (subject 8).

These effects are considered to be effects of stabilizing the grounding of the toes, correcting body distortion, and stabilizing the center of gravity as a result of wearing the correction devices of the present invention. The correction device of the present invention is characterized in that the distortion of the body is continuously corrected during the process of working and moving daily life with continuous wearing.

The effect of the toe band of the present invention was measured by measuring the pressure on the sole using a plantar pressure distribution measuring apparatus Foot Look (manufactured by LaContul Co., Ltd.). The state of foot pressure distribution before and after wearing about a person with frozen shoulders, right leg knee pain and left hip pain is shown in FIGS. 4 to 6, respectively. As shown in the figures, it can be seen that the contact pressure (body weight) of the sole is applied more uniformly after wearing than before wearing. In addition to that, the person with frozen shoulders (FIG. 4) becomes to be able to raise up his left hand. A person with knee pain in the right foot (FIG. 5) can be free of supporters, making it easier for the person to ascend and descend stairs. Although the person with left hip pain (FIG. 6) was inclined because of that, the person became able to put weight on the left foot, and the body's inclination got better, and the person became able to climb up and down the stairs without having a handrail. From these, it can be seen that the toe band of the present invention has the effect of curing frozen shoulder, knee pain and hip pain.

(Buttocks lift experiment) The nine female subjects (at the age of 30s to 40s, the twisting bands of the present invention were respectively worn on the middle fingers of both feet so as to twist to the thumb side viewed from above. As a result, nine out of nine people felt that their buttocks lifted. Therefore, questionnaires were taken on the feeling of the people in 10 levels from 1 to 10. They evaluated under the condition of 5 when not worn. A survey of visual impressions was taken from people around them (Table 2).

TABLE 2

| | Feeling of hip up | | Impression of the person | Surrounding impressions |
|---|---|---|---|---|
| subject | Before wearing | After wearing | (after wearing) | (after wearing) |
| A | 5 | 8 | Feeling that the center of gravity goes forward. My waist, warps too much. | the weight goes forward and fall forward in appearance |
| B | 5 | 8 | I felt that my waist was bent. | in appearance, in case of primarily raised buttocks, the weight felt to go forward after wearing |
| C | 5 | 7 | I felt that my waist was bent. Feeling that the center of gravity went forward. | butt got in the middle in appearance |
| D | 5 | 6 | the right side of buttocks which was hanging felt lifted | Right butt rised in appearance |
| E | 5 | 7 | Feeling that the meat of the butt decreased. | butt went up to the middle in appearance |
| F | 5 | 7 | When worn on both sides the difference in height of the buttocks widens. | The same impression by those looking, in appearance, when woen on hangind side, heights of buttocks became even |
| G | 5 | 8 | I feel that the center of my buttocks has been tighten and lifted. | It looks like the buttocks are up. |

TABLE 2-continued

| subject | Feeling of hip up | | Impression of the person (after wearing) | Surrounding impressions (after wearing) |
|---|---|---|---|---|
| | Before wearing | After wearing | | |
| H | 5 | 6 | I feel like buttocks lifted. I feel that buttocks got close to the center. | It looks like the buttocks are up. |
| I | 5 | 6 | I felt that my buttocks lifted. | It looks like the buttocks are up. |

As a result, among 9 subjects, 8 were 3, 7 were 3 and 6 were 3. There were no subjects with 5 or less evaluation which is the level before wearing. Seeing the impressions of the people themselves, impressions were obtained such that: the center of gravity goes forward; the waist bended backward; the buttocks hanging down was raised; meat in the buttocks decreased; when put on both sides, the difference in the height of the buttocks widens (it will be even if put on to the hanging side); the center of my buttocks has felt tighten and lifted; felt that the buttocks come close to the center.

Impressions from the surroundings were also obtained as follows: to put the weight forward and to lean forward in appearance; the buttocks come close to the center; (the right side of the buttocks was hanging) it looks like the right side raised; buttocks come to center and lifted in appearance; it looks like buttocks heights get even when put on the hanging side; feeling that the buttocks lifted in appearance. When the other person touched on the subject's buttocks, the person felt the buttocks were firm, came close and lifted in appearance. Photographs of before-after are shown in FIGS. 7-9. Apparently, the weight is put on the front and the body leans forward. It can be observed that the buttocks rise if watched well. FIG. 10 is a view from the back, and it can be seen that the buttocks lifted from the wrinkles of the pants.

Theoretically, it is speculated as followings. By tightening the meridians, the large lumbar muscles become tense, and the action of attracting the femoral head to the center works, when the iliac muscle is tensed, the pelvis is tilted forward. By the two actions, it is thought that the center of gravity goes to the front, and it is felt as if the buttocks got in the middle and got raised.

INDUSTRIAL APPLICABILITY

The present invention is applicable to the health industry, the manufacturing industry of health instruments, and the like.

DESCRIPTION OF THE REFERENCE NUMERALS

1 outer circumference of a cylinder
2 inner circumference of a cylinder

The invention claimed is:

1. A method for improving a flexibility of a body, or for reducing or treating one or more symptoms selected from the group consisting of bow legs, spine strain, pelvic strain, and center of gravity shift, comprising:
 wearing a correction device on a toe, and
 twisting the correction device in one direction on the toe,
 wherein the correction device is a closed continuous cylindrical correction device for a toe, comprising triangular prism shaped protrusions into an inner direction on an inner peripheral portion, and all inner edges of the triangular prism shaped protrusions are inclined in a same one direction with respect to a circumference to twist in the one direction.

2. A method of lifting buttocks, comprising:
 wearing a correction device on a middle toe, and
 twisting the correction device in one direction on the toe,
 wherein the correction device is a closed continuous cylindrical correction device for a toe, comprising triangular prism shaped protrusions into an inner direction on an inner peripheral portion, and all inner edges of the triangular prism shaped protrusions are inclined in a same one direction with respect to a circumference to twist in the one direction.

* * * * *